United States Patent [19]
Johnson

[11] Patent Number: 4,536,180
[45] Date of Patent: Aug. 20, 1985

[54] SURGICAL INSTRUMENT FOR SUCTION LIPOLYSIS

[76] Inventor: Gerald W. Johnson, 17070 Red Oak, #301, Houston, Tex. 77090

[21] Appl. No.: 516,038

[22] Filed: Jul. 22, 1983

[51] Int. Cl.³ .............................................. A61M 27/00
[52] U.S. Cl. .................................... 604/268; 604/119; 604/902
[58] Field of Search ................ 604/268, 119, 902, 43, 604/45

[56] References Cited

U.S. PATENT DOCUMENTS

| | | | |
|---|---|---|---|
| 2,097,039 | 10/1937 | Peterson | 604/268 X |
| 2,667,682 | 2/1954 | Stone | 604/268 X |
| 3,999,554 | 12/1976 | Kim et al. | 604/268 X |

Primary Examiner—Stephen C. Pellegrino
Attorney, Agent, or Firm—Neal J. Mosely

[57] ABSTRACT

A surgical instrument for use in suction lipolysis consists of a long, narrow tube having a pointed or tapered closed end, for insertion into the body, and being open at the other end for connection to a source of vacuum. The tube has a side opening adjacent to the closed end for entry of fatty material during use. A passageway is provided, either as a separate passage inside the tube or a separate tube inside or outside the main tube, with an end opening inside the closed end of the main tube beyond the side opening. A handle surrounds and supports the main tube and passageway and includes a manually operated valve for venting the other end of the passageway or separate tube to allow air to enter the closed end portion of the main tube during use for clearing obstruction therein.

11 Claims, 5 Drawing Figures

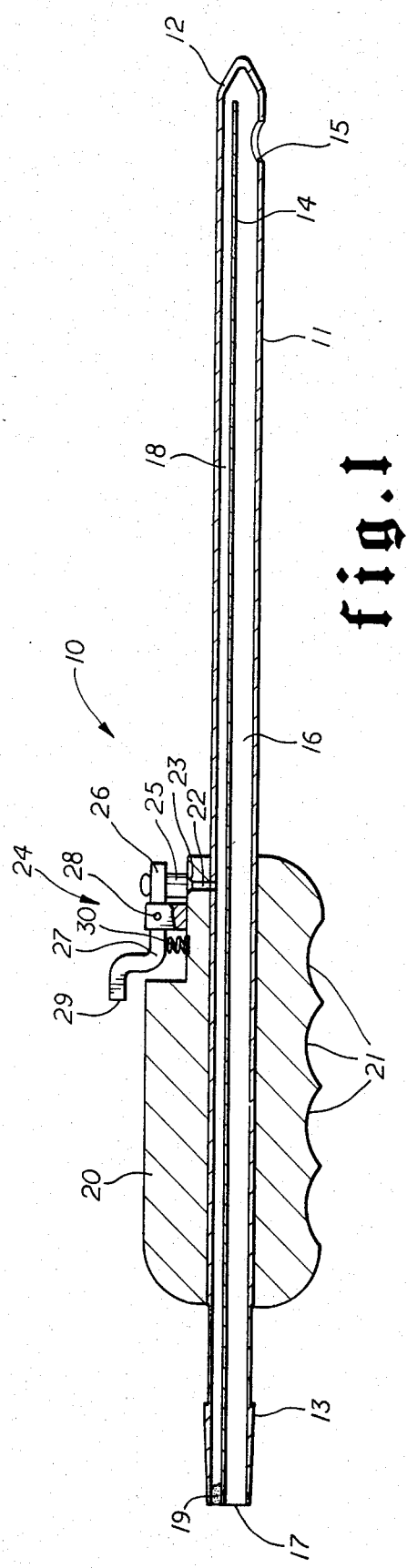
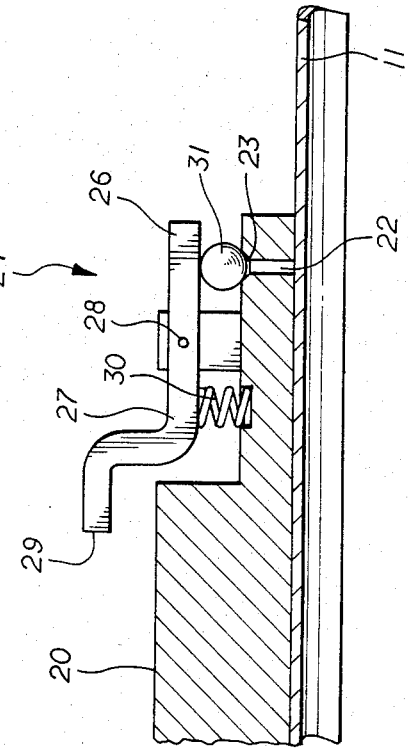
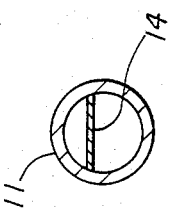

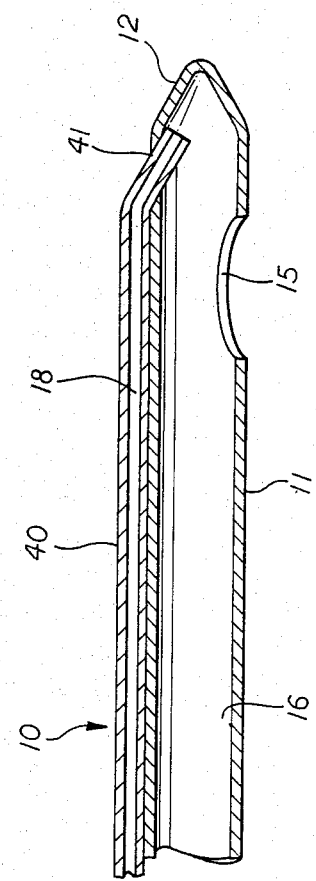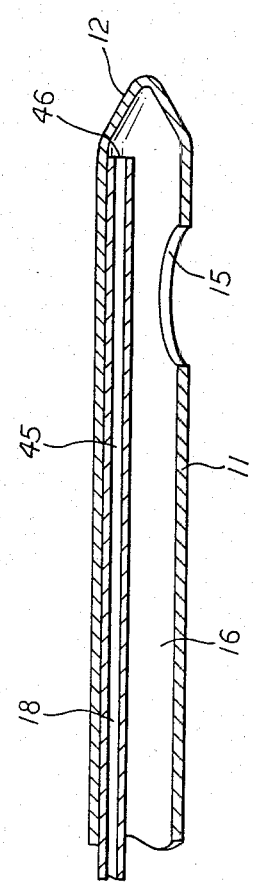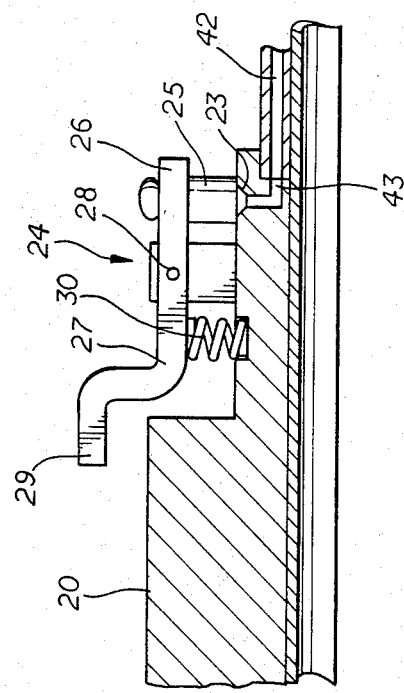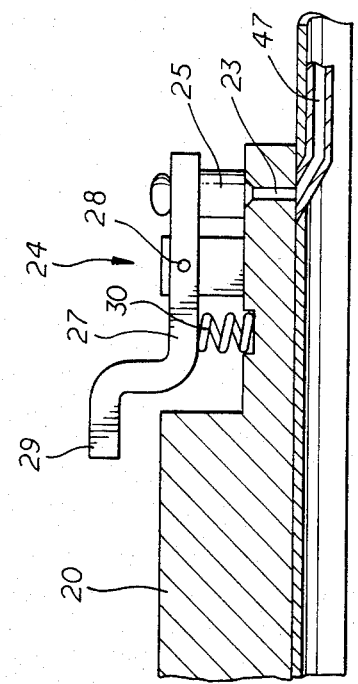

SURGICAL INSTRUMENT FOR SUCTION LIPOLYSIS

BACKGROUND OF THE INVENTION

1. Field of the Invention

This invention relates to the field of surgical instruments and more particularly to a surgical instrument for use in suction lipolysis.

2. Brief Description of the Prior Art

A number of different surgical appliances are known for applying vacuum to the area being treated for withdrawing bodily fluids during surgery or for other purposes.

Bridgman U.S. Pat. No. 3,804,089 discloses a vacuum curet for use with uterine aspirator apparatus. The curet has a cannula barrel with a suction port at one end, and a handle at the other. The equipment is designed to permit introduction of fluid during operative procedures.

Jenkins U.S. Pat. No. 1,987,907 discloses a combination surgical air-blast and suction tip. The device has twin tubes which are separately controlled and can apply either vacuum or an air-blast to a given area.

McLeod U.S. Pat. No. 2,449,497 discloses an improved aspirator for use in dentistry.

Tofflemire U.S. Pat. No. 2,812,765 discloses a combination aspirator and fluid delivering surgical instrument.

Meyer U.S. Pat. No. 3,085,573 discloses the surgical apparatus for applying either compressed air or vacuum to a given area for removing contaminating materials during surgery.

Noonan U.S. Pat. No. 3,109,426 discloses a combination aspirator and irrigation instrument.

Turner U.S. Pat. No. 3,208,145 discloses an aspirating handpiece with controls for vacuum, air and water for use in dentistry.

Stewart U.S. Pat. No. 3,749,090 discloses a combination surgical instrument for applying vacuum and for delivering fluid to a work area.

Phillips U.S. Pat. No. 4,299,221 discloses a tool for dental and surgical use which is constructed for irrigation or suction.

Recently, a surgical technique has been developed for removal of fatty deposits, sometimes known as cellulite, from selected areas of the body. This procedure, which is known as suction lipolysis, consists of making a surgical incision and inserting a tubular surgical instrument under the skin into the area from which fat is to be removed and applying vacuum to suck out fatty material. Surgical instruments for this purpose were developed in France and have had very little use in the United States. The surgical instrument presently used is a tubular member which has a closed end and a side opening. This instrument is inserted under the skin and suction applied at the end of the tube to draw fatty material through the tube. A difficulty has developed in the use of the surgical instrument which was originally developed for the surgical procedure. This difficulty is that the instrument is subject to plugging with bodily material being removed and there is no way to clear the plugging without removing the instrument from the body.

The various surgical and dental instruments described above have some features in common with the tools used in surgical lipolysis but are not constructed in a form permitting use for such a surgical procedure. There is nothing in any of these surgical tools which suggest any solution to the problem encountered where the tool becomes plugged with bodily materials during use.

SUMMARY OF THE INVENTION

An object of the invention is to provide a new and improved surgical instrument in use in suction lipolysis.

Another object of this invention is to provide an improved surgical instrument for use in lipolysis having a means for unplugging the instrument during use in surgery.

Still another to this invention is to provide an improved surgical instrument for suction lipolysis having a means to vent the tool or instrument beyond the point where bodily materials are sucked into it.

Another object of this invention is to provide a surgical instrument for use in suction lipolysis having one passageway connection to vacuum and another passageway controlled by a valve for variable venting of the tool during use.

Another object of this invention is to provide an improved surgical instrument for in use suction lipolysis consisting of a tubular instrument with a tapered end for insertion into the body and having a side opening into which bodily materials may be drawn by suction and a separate valve passageway for venting the instrument by introduction of air into the closed end portion.

Other objects of the invention will become apparent from time to time throughout the specification and claims as hereinafter related.

The above noted objects and other objects of the invention are accomplished by a surgical instrument for use in suction lipolysis which consists of a long, narrow tube having a pointed or tapered closed end, for insertion into the body, and being open at the other end for connection to a source of vacuum. The tube has a side opening adjacent to the closed end for entry of fatty material during use. A passageway is provided, either as a separate passage inside the tube or a separate tube inside or outside the main tube, with an end opening inside the closed end of the main tube beyond the side opening. A handle surrounds and supports the main tube and passageway and includes a manually operated valve for venting the other end of the passageway or separate tube to allow air to enter the closed end portion of the main tube during use for clearing obstruction therein.

BRIEF DESCRIPTION OF THE DRAWINGS

FIG. 1 is a view in longitudinal central section of one embodiment of a surgical instrument for use in suction lipolysis according to this invention.

FIG. 2 is a sectional view on the line 2—2 of FIG. 1.

FIG. 3 is an enlarged detail sectional view of another venting valve arrangement of the surgical instrument.

FIG. 4 is a longitudinal sectional view, broken along its length, of another embodiment of the surgical instrument.

FIG. 5 is a longitudinal sectional view, broken along its length, of still another embodiment of the surgical instrument.

DESCRIPTION OF THE PREFERRED EMBODIMENT

Suction lipolysis is a surgical removal of localized "fatty deposits". These "fatty deposits" do not respond to conventional methods of weight reduction. The surgical technique, known as suction lipolysis, has been performed in Paris, France over the past six years. It is an excellent and permanent method of removing stubborn areas of localized adipose tissue, commonly called "cellulite".

Cellulite is non medical term often used to describe a certain form of body fat. Cellulite is a term used by the lay person to describe problem areas of localized fatty deposits. Body fat varies in different areas of the body. Throughout the body, there is fat under the skin. These fat cells are arranged to form a thin blanket-like layer. In certain areas of the body, fat cells exist in a more dense manner. This fat is arranged in a globular form rather than a blank form. The fat cells act as balloons and can store a large amount of fat. It is this type of fat cell which has commonly become known as "cellulite".

The removal of these "fatty deposits" is difficult if not impossible, to obtain by ordinary methods of weight control. Permanent removal of these fat cells has required surgical procedures. Previously, it was necessary to make large incisions in order to remove localized fatty deposits. This method was often discouraged due the conspicuous skin scars which were necessary. At present, the most effective removal of "fatty deposits" is called suction lipolysis.

In suction lipolysis the patient is first positioned properly and the selected means of anesthetic administered. Saline plus an enzyme is injected into the operative area. The saline helps to overfill the fat cells and cause a momentary rupture of these cells. Shorty after the saline is injected, a very small incision is made in the problem area. A long, smooth, hollow surgical instrument is inserted under the skin into the problem area and the fat cells are suctioned out.

This procedure can be done on an inpatient or outpatient basis. This decision remains up to the physician and patient. The anesthesia used is determined by the size of the area and amount of fatty tissue to be removed. Sometimes a local anesthetic only is enough, while at other times general anesthesia is required. In the immediate postoperative period, some degree of discomfort is encountered. Most often, only a mild discomfort is encountered. Analgesics are prescribed for this discomfort. An elastic bandage is applied to the operative site for about seven days. This bandage applies a small amount of pressure to help minimize bruising and swelling.

The surgery can be repeated but is permanent in its effect. It may be necessary at a later date to repeat the procedure in order to obtain symmetry. Once the fat has been removed, the skin in the operative area usually will shrink to conform to the body contour. In some cases, however, it may be necessary to remove excessive skin surgically.

In the accompanied drawings, there are shown different embodiments of the surgical instrument used in the procedure of suction lipolysis described above. In FIGS. 1 and 2 there is shown one embodiment of the surgical instrument 10 used for suction lipolysis.

Surgical instrument 10 consist of an elongated tube 11 of small cross section having closed end portion 12 which is tapered or pointed to a round tip. Tube 11 has an end portion 13 arranged for connection to a vacuum line (not shown). Tube 11 is provided with a elongated plate or divider member 14 which extends from end portion 13 to a point just short of the closed end 12 of the tube. An opening 15 is provided in the side wall of tube 11.

Divider member 14 divides the interior of tube 11 into a suction passage 16 which extends from the open end 17 of the tube to the side opening 15 at the closed end portion 12; and a venting passage 18 which extends from a closed end 19 to the end of divider 14. Passages 16 and 18 communicate around the of wall member 14.

Tube 11 extends and is secured in a handle 20 which has finger grips 21 on the same side as the side opening 15 of the closed end portion 12 of tube 11. A small passage 22 opens through the wall of tube 11 and connects venting passage 18 to an opening 23 which controlled by a valve apparatus 24.

Valve apparatus 24 comprises a valve member 25, constructed in the same manner as the spit valve on a musical instrument, secured on one end 26 of a lever or actuator 27. Lever or actuator 27 is supported on pivot 28. The end portion 29 of lever or actuator 27 is rebent to facilitate operation by the thumb of the surgeon. A spring 30 is provided which biases the lever or actuator 27 to move valve member 25 to a position closing the opening 23. In FIG. 3, there is shown an alternate form of valve apparatus 24 which uses a ball valve 31 instead of the valve member 25. Ball valve 31 is spherical in shape and is secured to the end portion 26 of valve operator 27.

In operation, the surgical instrument 10 has end portion 13 connected to a source of vacuum which is controllable. The surgical procedure described above is carried out and the end portion 12 of tube 11 is inserted through the surgical incision into the area from which fat cells are to be withdrawn. On application of vacuum at the end opening of 17 the fat cells are drawn through side opening 15 into passage 16 for withdrawal from the fatty layer under the skin.

If hard or fibrous material is encountered or other material which may plug the passage 16, the instrument can be cleared without removing it from the surgical area. In such a case, the surgeon presses on the end portion 29 of operator 27 to open valve member 25. This allows air to bleed in through passage 22 to passage 18. The air bleeds into the end portion 12 of tube 11 around the end of the divider member 14 at a point beyond the side opening 15. The application of air at this end portion beyond the point were the plug has occurred allows the vacuum applied at the other end to pull the plug material on through without having to continue to pull on the bodily material adjacent to the side opening 15. As soon as the instrument is cleared the valve is allowed to close and further suctioning of fatty material is continued.

ANOTHER EMBODIMENT

In FIG. 4 there is shown another embodiment of the surgical instrument 10 used for suction lipolysis in which the air venting passage is a separate tube exterior to the main tube 11. The instrument is otherwise identical to the instrument shown in FIG. 1.

In this embodiment, a small-diameter tube 40 extends along the outside of the main tube 11 and through an opening 41 into the end of the tube at a point just short of the closed end 12. The interior of tube 11 provides a suction passage 16 which extends from the open end of the tube to the side opening 15 at the closed end portion 12. Small-diameter tube 40 provides a venting passage 18 which extends from an end 42, adjacent to the handle, to the interior of the closed end portion 12 of tube 11.

Tube 11 extends and is secured in a handle 20 as described above. A small passage 43 opens through the end of handle 20 and connects venting passage 18 to opening 23 which is controlled by a valve apparatus 24 which is identical to that described for FIG. 1.

In operation, this embodiment of the surgical instrument 10 functions the same as the embodiment described and shown in FIG. 1.

If hard or fibrous material is encountered or other material which may plug the passage 16, the instrument can be cleared without removing it from the surgical area. In such a case, the surgeon presses on the end portion 29 of operator 27 to open valve member 25. This allows air to bleed in through passage 22 to passage 18 in small-diameter tube 40. The air bleeds into the end portion 12 of tube 11 around the end of the divider member 14 at a point beyond the side opening 15 as in the previously described embodiment. The application of air at this end portion beyond the point were the plug has occured allows the vacuum applied at the other end to pull the plug material on through without having to continue to pull on the bodily material adjacent to the side opening 15. As soon as the instrument is cleared the valve is allowed to close and further suctioning of fatty material is continued.

A FURTHER EMBODIMENT

In FIG. 5 there is shown another embodiment of the surgical instrument 10 used for suction lipolysis in which the air venting passage is a separate tube positioned inside the main tube 11. The instrument is otherwise identical to the instrument shown in FIG. 4.

In this embodiment, a small-diameter tube 45 extends along the inside of the main tube 11 and has an open end 46 at a point just short of the closed end 12. The interior of tube 11 provides a suction passage 16 which extends from the open end of the tube to the inside opening 15 at the closed end portion 12. Small-diameter tube 40 provides a venting passage 18 which extends from an end 47, adjacent to the handle, to the interior of the closed end portion 12 of tube 11.

Tube 11 extends through and is secured in a handle 20 as described above. The end 47 of small-diameter tube 45 extends through the wall of tube 11 inside the handle 20 and connects venting passage 18 to opening 23 which is controlled by a valve apparatus 24 which is identical to that described for FIG. 4.

In operation, this embodiment of the surgical instrument 10 functions the same as the embodiment described and shown in FIG. 4.

If hard or fibrous material is encountered or other material which may plug the passage 16, the instrument can be cleared without removing it from the surgical area. In such a case, the surgeon presses on the end portion 29 of operator 27 to open valve member 25. This allows air to bleed in through passage 23 to passage 18 in small-diameter tube 45. The air bleeds into the end portion 12 of tube 11 around the end of the divider member 14 at a point beyond the side opening 15 as in the previously described embodiment. The application of air at this end portion beyond the point were the plug has occured allows the vacuum applied at the other end to pull the plug material on through without having to continue to pull on the bodily material adjacent to the side opening 15. As soon as the instrument is cleared the valve is allowed to close and further suctioning of fatty material is continued.

I claim:

1. A surgical instrument for use in suction lipolysis on living human beings, comprising
    an elongated tube having one end with a tapered, substantially pointed, closed end having a round tip of a size and shape for insertion under the skin, and another end open for connection to a vacuum source,
    said tube having an opening on one side only at said one end a short distance from said pointed round tip closed end,
    a handle surrounding and secured to the other end of said tube, with a sufficient amount of the tube behind the handle for connection to a vacuum source,
    a passageway means having an open end adjacent to said handle and extending longitudinally of said tube, along the side opposite to said side opening, adjacent to the passage therein and having an end opening into said tube adjacent to the inside of said pointed round tip closed end at a point beyond said tube side opening, and
    valve means supported on said handle on the side opposite to said side opening, having a position normally closing said passageway means open end, and moveable to open and close said passageway means to control introduction of air to the closed end of said tube for clearing obstruction during use.

2. A surgical instrument according to claim 1 in which
    said tube has a wall member extending longitudinally for substantially the entire length thereof to a point just short of said pointed round tip closed end, but beyond said side opening, said wall member dividing said tube into a pair of separate passages,
    one of said passages extending along said wall member from said side opening at one end to said open end for vacuum connection at the other end,
    the other of said passages being closed at a point adjacent to said tube open end and extending along said wall member,
    said one passage and said other passage communicating around the end of said wall member,
    said other passage comprising said passageway means and having the open end thereof opening through the wall of said tube adjacent to said handle on the side opposite to said side opening, and
    said valve means comprising a spring-loaded valve member closing the open end of said passageway and having a valve operating member supporting the same on said handle.

3. A surgical instrument according to claim 2 in which
    said valve operating member comprises a lever member pivotally supported on said handle and extending over said passageway means open end,
    said valve member being supported on and moveable by said lever, and
    spring means cooperable with said lever and positioned to rotate the same in a direction engaging said valve member with said passageway means open end to close the same.

4. A surgical instrument according to claim 1 in which
    said handle is shaped with finger grips on the same side as said tube side opening.

5. A surgical instrument according to claim 4 in which
said valve means is positioned on the opposite side of said handle from said finger grips.

6. A surgical instrument according to claim 1 in which
said passageway means comprises a separate tube member extending longitudinally of said tube along the side opposite said side opening having one open end inside said tube just short of said pointed round tip closed end, but beyond said side opening, and another open end adjacent to said handle,
said valve means comprising a spring-loaded valve member closing the open end of said passageway adjacent to said handle and having a valve operating member supporting the same on said handle.

7. A surgical instrument according to claim 6 in which
said valve operating member comprises a lever member pivotally supported on said handle on the side opposite said side opening and extending over said passageway open end,
said valve member being supported on and moveable by said lever, and
spring means cooperable with said lever and positioned to rotate the same in a direction engaging said valve member with said passageway open end to close the same.

8. A surgical instrument according to claim 6 in which
said handle is shaped with finger grips on the same side as said tube side opening.

9. A surgical instrument according to claim 8 in which
said valve means is positioned on the opposite side of said handle from said finger grips.

10. A surgical instrument according to claim 6 in which
said separate tube member extending longitudinally of the interior said tube having one open end inside said tube just short of said pointed round tip closed end, but beyond said side opening, and another open end opening laterally outward through the tube adjacent to said handle.

11. A surgical instrument according to claim 6 in which
said separate tube member extending longitudinally of said tube along the exterior surface thereof, having one end extending inside said tube and open at a point just short of said pointed round tip closed end, but beyond said side opening, and another end with an opening laterally outward relative to the tube adjacent to said handle and providing a valve opening closable by said valve means.

* * * * *